(12) United States Patent
Shimura

(10) Patent No.: US 8,879,821 B2
(45) Date of Patent: Nov. 4, 2014

(54) DEFECT INSPECTING DEVICE AND DEFECT INSPECTING METHOD

(75) Inventor: Kei Shimura, Mito (JP)

(73) Assignee: Hitachi High-Technologies Corporation, Tokyo (JP)

(*) Notice: Subject to any disclaimer, the term of this patent is extended or adjusted under 35 U.S.C. 154(b) by 170 days.

(21) Appl. No.: 13/520,479

(22) PCT Filed: Dec. 27, 2010

(86) PCT No.: PCT/JP2010/073558
§ 371 (c)(1),
(2), (4) Date: Jul. 3, 2012

(87) PCT Pub. No.: WO2011/089829
PCT Pub. Date: Jul. 28, 2011

(65) Prior Publication Data
US 2013/0011043 A1 Jan. 10, 2013

(30) Foreign Application Priority Data
Jan. 22, 2010 (JP) .................................. 2010-012362

(51) Int. Cl.
*G06K 9/00* (2006.01)
*G01N 21/956* (2006.01)
*G01N 21/95* (2006.01)

(52) U.S. Cl.
CPC .. *G01N 21/95623* (2013.01); *G01N 2021/9513* (2013.01); *G01N 2021/95638* (2013.01)
USPC .......................................... 382/145; 382/152

(58) Field of Classification Search
USPC ................................................. 382/145, 149
See application file for complete search history.

(56) References Cited

U.S. PATENT DOCUMENTS

| 6,031,607 A * | 2/2000 | Miyazaki ................... 356/237.1 |
| 7,031,511 B2 * | 4/2006 | Asai ............................... 382/149 |
| 7,111,943 B2 * | 9/2006 | Agostinelli et al. ............ 353/79 |

(Continued)

OTHER PUBLICATIONS

Japanese Office Action mailed Mar. 19, 2013 in corresponding Japanese Patent Application No. 2010-012362 with English language translation.

(Continued)

*Primary Examiner* — Gregory M Desire
(74) *Attorney, Agent, or Firm* — Brundidge & Stanger, P.C.

(57) ABSTRACT

The present invention provides a defect inspection system which enables an improvement in the efficiency of spatial filter settings, and at the same time enables automation of the spatial filter settings. An adjustable field-of-view diaphragm is narrowed to obtain an image of a spatial filter surface by use of an observation camera, and pixels of the image are classified into a plurality of groups according to the brightness level of bright spots of diffracted light. A spatial filter is set in such a manner that a group, the brightness level of which is highest, is light-shielded, and an observation image is then captured. Whether or not a repetitive pattern remains in the captured image is determined, and when it is determined that a repetitive pattern remains, the settings of the spatial filter are changed. The spatial filter is set in such a manner that in addition to the group which has been light-shielded earlier, a group, the brightness level of which is the highest next to the light-shielded group, can also be light-shielded. The same step is repeated until it is determined that no repetitive pattern remains. The settings of the spatial filter then end.

18 Claims, 10 Drawing Sheets

(56) References Cited

U.S. PATENT DOCUMENTS

| | | | |
|---|---|---|---|
| 7,436,507 B2 * | 10/2008 | Moribe | 356/237.4 |
| 7,528,942 B2 | 5/2009 | Nakano et al. | |
| 2007/0057184 A1 * | 3/2007 | Uto et al. | 250/310 |
| 2009/0059216 A1 | 3/2009 | Shibata et al. | |

OTHER PUBLICATIONS

Japanese Office Action mailed Jun. 18, 2013 in corresponding Japanese Patent Application No. 2010-012362 with English language translation.

* cited by examiner

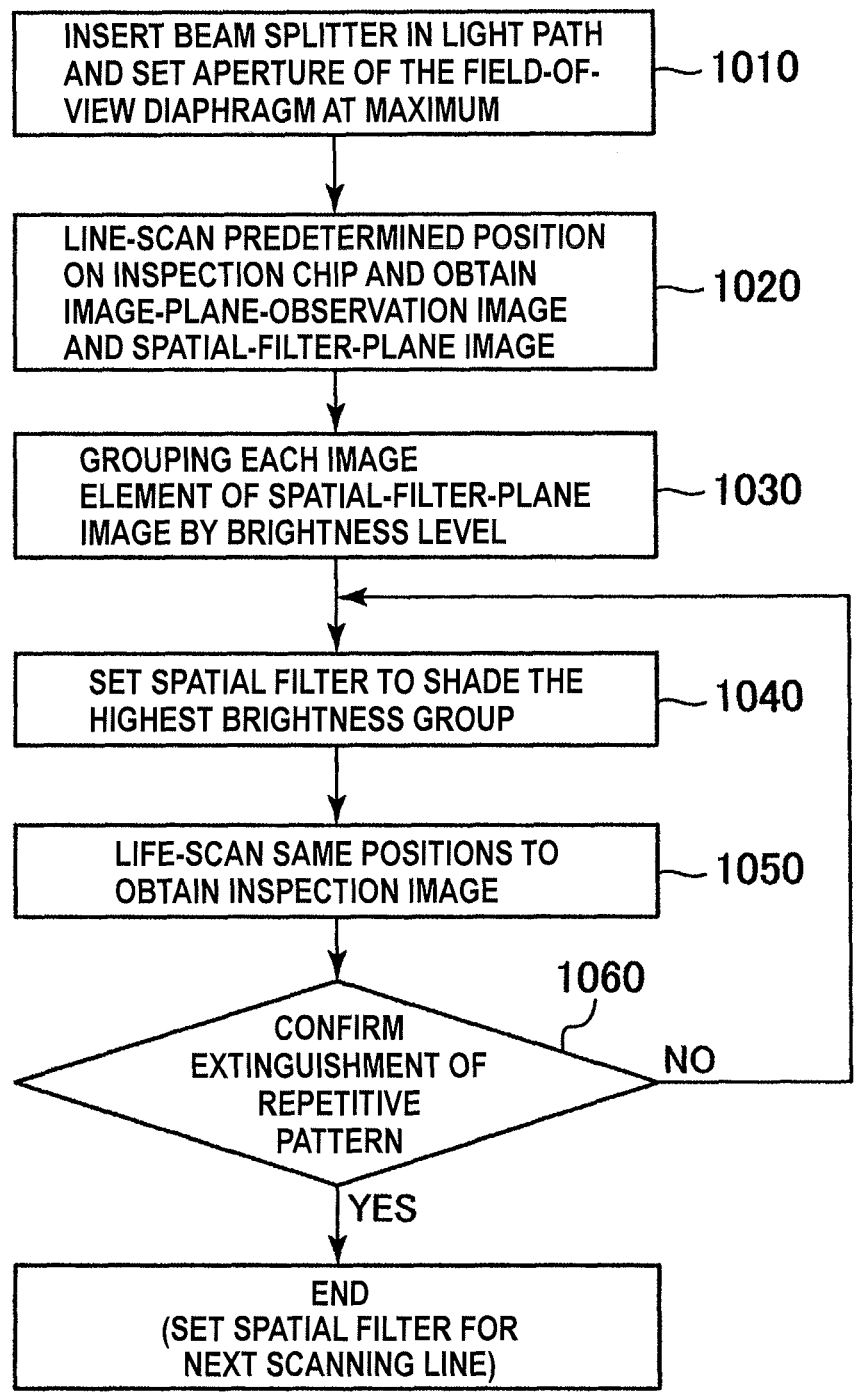

DEFECT INSPECTING DEVICE AND DEFECT INSPECTING METHOD

TECHNICAL FIELD

The present invention relates to a defect inspection system for detecting a defect such as a foreign matter and a deformed pattern in a manufacturing process of a product such as a semiconductor device, a liquid crystal display device and a printed circuit board, which substrates are each formed with a pattern. The invention also relates to a defect inspection method thereof.

BACKGROUND ART

In a semiconductor manufacturing process, a foreign matter on a semiconductor substrate (wafer) may cause a failure such as a failure in insulation of wiring and a short circuit thereof. With the progress of miniaturization of patterns on semiconductor devices, a minute foreign matter in a semiconductor substrate may cause a failure in insulation of a capacitor, breakage of a gate oxide film or the like.

Likewise, a liquid crystal display device manufacturing process involves existence of a foreign matter on a pattern or occurrence of some defects on a shape of the pattern. Such a foreign matter or defects will disable the use of the device as a display device.

Further, the above is true for the case of a manufacturing process of printed circuit boards. A foreign matter mixed in the manufacturing process may cause a short circuit in a pattern, and a poor connection thereof.

Patent Document 1 discloses an example of a technique for detecting a foreign matter on this kind of substrate. To be more specific, according to the technique disclosed in Patent Document 1, a semiconductor substrate is irradiated with laser light to detect scattered light from a foreign matter which adheres to the semiconductor substrate, and the scattered light is detected and the signal is compared with the inspection result of the same kind of semiconductor substrate which has been subjected to the immediately preceding inspection. Comparing the detected signal with the inspection result makes it possible to eliminate a false report caused by a pattern, thereby enabling inspection of a foreign matter and a defect with high sensitivity and high reliability.

In addition, as the technique for inspecting a foreign matter, there is known a method in which a wafer is irradiated with coherent light, and light radiated from a repetitive pattern on the wafer is removed by a spatial filter, and a foreign matter and a defect which do not have repeatability are emphasized to detect the foreign matter and the defect.

Moreover, Patent Document 2 discloses a foreign matter inspection system, wherein a circuit pattern formed on a wafer is irradiated from a direction inclined by 45° with respect to a main straight line group of this circuit pattern to prevent a zero-order diffracted light from the main straight line group from entering an aperture of an objective lens of a detection optical system.

Furthermore, Patent Document 3 discloses a technique in which the inspection sensitivity is improved by most suitably setting a spatial filter for each area on a wafer to perform inspection.

PRIOR ART DOCUMENTS

Patent Documents

Patent Document 1: JP-1987-89336-A
Patent Document 2: JP-1989-117024-A
Patent Document 3: JP-2004-184142-A

SUMMARY OF THE INVENTION

Problems to be Solved by the Invention

Incidentally, as semiconductor devices are provided with higher functions, patterns formed on one semiconductor device become more complicated. Consequently, patterns having a plurality of repeated cycles are frequently mixed.

When such a semiconductor device is inspected, it is difficult to make condition settings of a spatial filter. Therefore, it takes long a time to complete the condition settings, and the optimization also becomes difficult.

In addition, even in the case of a semiconductor device having a relatively simple structure such as a memory, human intervention is required for setting of the conditions of a spatial filter; therefore it has been difficult to improve the efficiency of spatial filter settings.

An object of the present invention is to implement a defect inspecting method which enables an improvement in the efficiency of spatial filter settings, and at the same time enables automation of the spatial filter settings, and a defect inspection system using the method.

Means for Solving the Problems

In order to achieve the above-described object, the present invention is configured as below.

One aspect of the present invention provides a defect inspection system and a defect inspection method. The defect inspection method includes the steps of: irradiating an object to be inspected with light; collecting reflected and scattered light from the object to be inspected by use of a detection lens while the object to be inspected is moved; capturing the image which is formed on a sensor with the light selectively transmitted through a spatial filter located in the detection lens; and at the same time, capturing the image of the spatial filter by an image sensor. The method further includes the steps of: displaying an image of a pattern formed on the surface of the object to be inspected and the image of the spatial filter plane on a spatial filter setting screen, and setting light shielding conditions of the spatial filter; capturing an image of the object to be inspected by use of the image sensor under the set conditions again while the object to be inspected is moved; and subjecting the captured image to comparison processing to detect a foreign matter or a pattern defect on the object to be inspected.

Effects of the Invention

According to the present invention, a defect inspecting method and a defect inspection system using the method can be implemented which enable an improvement in the efficiency of spatial filter settings, and at the same time enable automation of the spatial filter settings.

BRIEF DESCRIPTION OF THE DRAWINGS

FIG. 9 is a flowchart illustrating automation steps of spatial filter settings according to a second embodiment of the present invention.

MODES FOR CARRYING OUT THE INVENTION

Embodiments of the present invention will be described below with reference to the accompanying drawings.

First Embodiment

Figure 1:
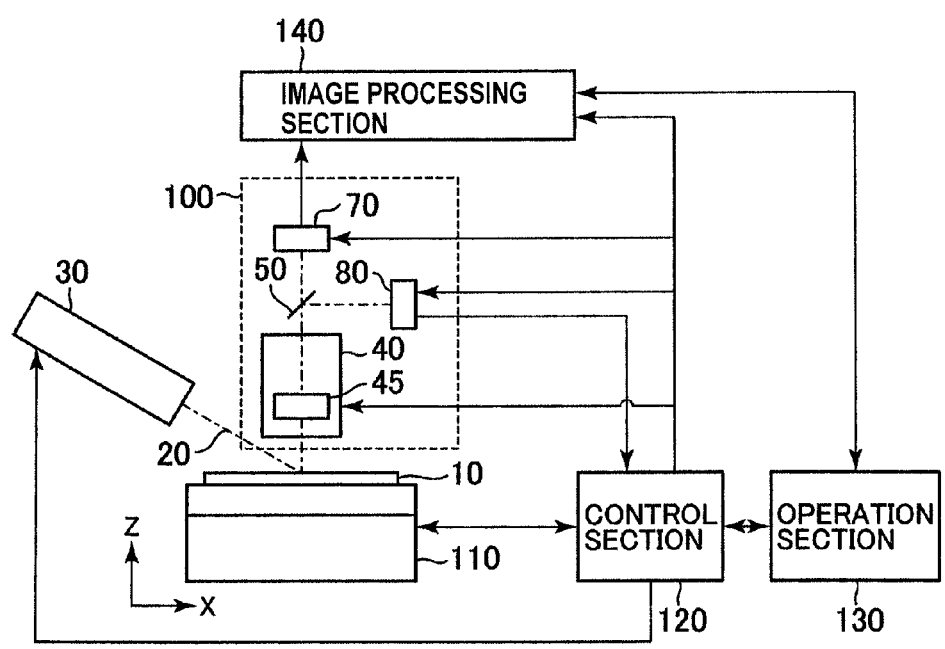
FIG. 1 is a diagram illustrating an overall configuration of a defect inspection system to which the present invention is applied.
Figure 2:
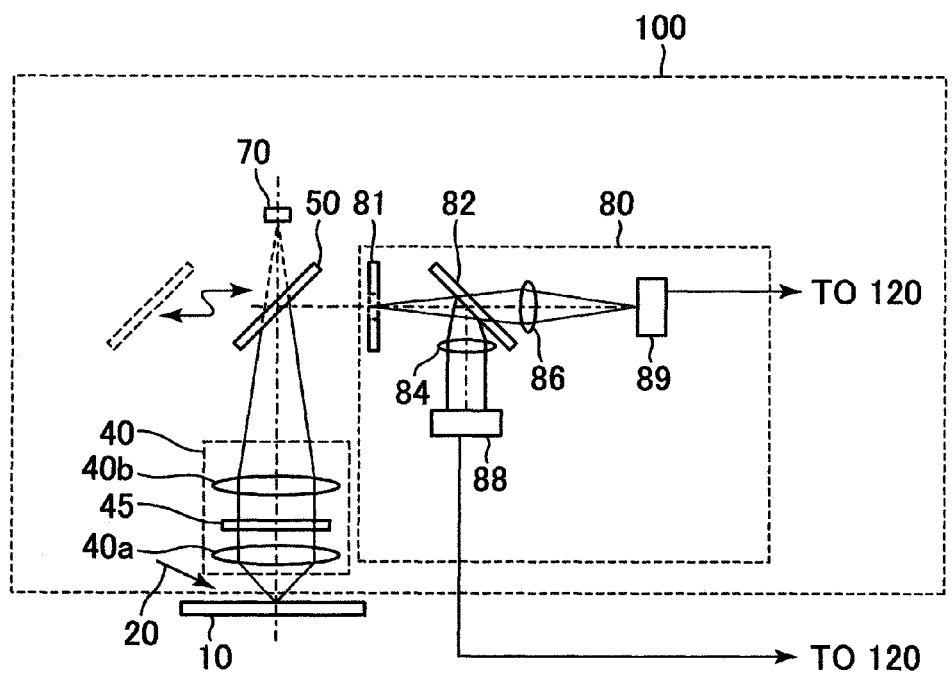
FIG. 2 is a diagram illustrating an example of a configuration of an inspection optical system in the defect inspection system shown in FIG. 1.

FIG. 1 is a diagram illustrating an overall configuration of a defect inspection system to which the present invention is applied. FIG. 2 is a diagram illustrating a configuration of an inspection optical system of the defect inspection system shown in FIG. 1. In addition, FIG. 3 is a diagram illustrating an example of an object to be inspected by the defect inspection system.

First of all, the example of the object to be inspected will be described with reference to FIGS. 3A and 3B.

Figure 3A:
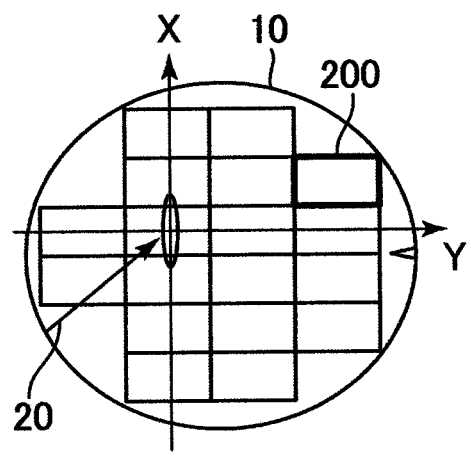
FIG. 3A is a diagram illustrating an example of a substrate to be inspected which is observed according to the present invention.

In FIG. 3A, the object to be inspected is a disc-like semiconductor wafer 10 in which logic LSI chips (or memory LSI chips) 200 are two-dimensionally arranged at specified intervals. The surface of the semiconductor wafer 10 is irradiated with illumination light 20.

Figure 3B:
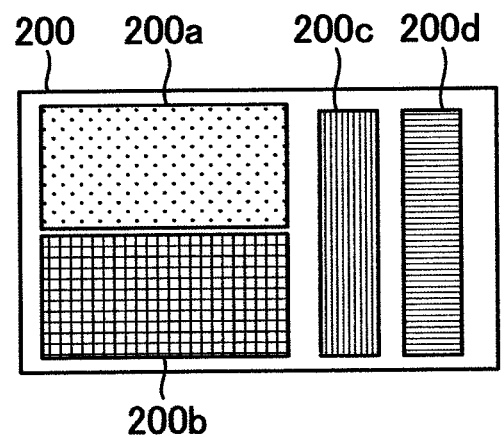
FIG. 3B is a diagram illustrating an example of a substrate to be inspected which is observed according to the present invention.

As shown in FIG. 3B, the chip 200 is formed mainly with memory cell regions 200a, 200b, peripheral circuit regions 200c, 200d (including a decoder and a control circuit), and the other regions.

The memory cell regions 200a, 200b are formed in such a manner that memory cell patterns, the minimum line width of which is, for example, about 0.03 to 0.1 micrometers, are two-dimensionally and regularly arranged (repeated). In addition, non-repetitive patterns, the minimum line width of which is, for example, about 0.1 to 0.4 micrometers, are formed on the peripheral circuit regions 200c, 200d.

Moreover, the other regions include, for example, a bonding area region (the minimum line width is, for example, ten micrometer order, and substantially no pattern).

Next, the defect inspection system will be described with reference to FIG. 1.

In FIG. 1, the object to be inspected 10 (a semiconductor wafer, a display element, a printed circuit board or the like) is placed on a stage 110. The stage 110 is configured to use, for example, an XY stage, a Z stage and a theta stage in combination.

The stage 110 is capable of scanning the object to be inspected 10 in the XY plane so as to enable an inspection optical system 100 provided above the stage 110 to inspect the whole surface of the object to be inspected 10. The object to be inspected 10 is irradiated with the illumination light 20 radiated from an illumination optical system 30 (including a light source).

Part of scattered and reflected light from a pattern and a defect (such as a foreign matter) on the object to be inspected 10 enters a detection lens 40, is introduced into a sensor 70 through a beam splitter 50 disposed immediately before an image plane of the detection lens 40, and at the same time is reflected by the beam splitter 50 to be introduced into an observation optical system 80.

The detection lens 40 is provided with a spatial filter 45 that is disposed on a spatial frequency plane inside the detection lens 40. It is possible to perform inspection with high sensitivity by using the spatial filter 45 to shield diffracted light from a repetitive pattern on the object to be inspected 10. A flat plate beam splitter which facilitates large-size implementation is used as the beam splitter 50.

The light incident on to the sensor 70 is photoelectrically converted into an image signal, and the image signal is transmitted to an image processing section 140. A detection lens provided with an analyzer may be used as the detection lens 40. A linear CCD sensor, a TDI sensor or the like is used as the sensor 70. The image processing section 140 compares images taken from adjacent identical patterns, and detects a defect on the basis of the difference obtained therefrom.

The observation optical system 80 is provided with: an image plane observation system capable of observing the image plane of the detection lens 40; and a spatial filter observation system capable of observing a plane of the spatial filter 45. The observation optical system 80 is used to set conditions of the spatial filter 45.

Next, in FIG. 2, the detection optical system 100 has a configuration from the object to be inspected 10 to the sensor 70 and the observation optical system 80.

The detection lens 40 is provided with an objective lens 40a and an imaging lens 40b; and the spatial filter 45 is disposed on a spatial frequency plane between both of the lenses 40a, 40b. As the spatial filter 45, for example, the following filters can be used: a filter in which rod-shaped light shielding objects are arranged lengthwise and crosswise, and the intervals therebetween are configured to be adjustable; and another filter in which pixels which are capable of shielding light are arranged on a two-dimensional array (a spatial light modulator which uses a liquid crystal or the like).

The beam splitter 50 is disposed immediately before the image plane of the detection lens 40, and is configured to be insertable/extractable into/from an optical path. In other words, the beam splitter 50 is configured to be movable, and can be disposed inside and outside the optical path. When conditions of the spatial filter 45 are set, the beam splitter 50 is inserted into the optical path of the detection lens 40, and the conditions are set while an image of an image plane and that of a spatial filter plane are observed by the observation optical system 80. In addition, at the time of inspection, the beam splitter 50 can be removed from the optical path of the detection lens 40 so as to prevent its influence on the image taking by the sensor 70.

The observation optical system 80 is provided with: an adjustable field-of-view diaphragm 81 which is disposed on the image plane of the detection lens 40, and limits a field-of-view; a beam splitter 82; a spatial filter surface observation lens 84; a spatial filter surface observation camera 88; an image plane observation lens 86; and an image plane observation camera 89.

An output image of the spatial filter surface observation camera 88 and that of the image plane observation camera 89 are transmitted to a control section 120 shown in FIG. 1. The control section 120 then sets the conditions of the spatial filter 45 on the basis of the transmitted images. The adjustable field-of-view diaphragm 81 defines a field-of-view at the time of image plane observation of the detection lens 40, and at the same time defines a region to be subjected to Fourier transform on the object to be inspected 10 at the time of spatial filter surface observation. This makes it possible to achieve one-to-one correspondence between a region on the object to be inspected 10 and the Fourier transform image thereof.

The image plane observation camera 89 observes an image of the adjustable field-of-view diaphragm 81, and an image of a region on the object to be inspected 10 which is observed through the aperture thereof.

Meanwhile, in this case, the image of the spatial filter surface observed by the spatial filter surface observation camera 88 becomes a Fourier transform image of the region on the object to be inspected 10 which is just observed in the aperture of the adjustable field-of-view diaphragm 81 by the image plane observation camera 89.

Therefore, the object to be inspected 10 is moved in such a manner that a region in which the spatial filter 45 is desired to be optimized comes to the center of the field-of-view of the image plane observation camera 89, and the aperture size of the adjustable field-of-view diaphragm 81 is adjusted through the operation section 130 in such a manner that the other regions do not come into the field-of-view, and the maximum aperture is allowed. This enables an operator to correctly know the diffracted light component which needs to be shielded.

Moreover, the spatial filter 45 is set by the operation section 130 and the control section 120 so as to shield diffracted light while an image of the spatial filter surface observation camera 88 is observed. This enables optimum condition settings of the spatial filter 45 for the region on the object to be inspected 10. The operation section 130 and the control section 120 constitute light shielding condition setting means.

Incidentally, configuring the imaging lens 40b to function as a zoom lens allows the operator to make a selection from among a plurality of image formation magnifications at the time of inspection. However, in such a case, it is desirable that the spatial filter plane observation lens 84 and the image plane observation lens 86 be also configured to be magnification adjustable. A magnification of the spatial filter surface observation lens 84 and that of the image plane observation lens 86 are set according to the focal length of the imaging lens 40b. This makes it possible to make effective use of the whole imaging surface of the spatial filter surface observation camera 88 and that of the image plane observation camera 89 when a spatial filter surface and an image plane are inspected.

Next, steps of setting conditions of the spatial filter 45 will be specifically described with reference to FIGS. 4, 5 and 6.

The optimum setting conditions of the spatial filter 45 depend on a shape of a repetitive pattern on the object to be inspected 10. Therefore, ideally, it is necessary to set the conditions for each region having a different pattern. The first embodiment of the present invention shows an example of a method for setting the spatial filter 45 which is the most suitable for a specific region (the region 200a on the chip 200).

First, the object to be inspected 10 is placed on the stage 110 so as to enable the image plane observation camera 89 to observe the repetitive pattern section 200a on the chip 200 (step 910). In this case, for example, as shown in FIG. 4, an operation screen 300 of the operation section 130 (shown in FIG. 1) is configured to display an image 310 of the image plane observation camera 89 and an image 320 of the spatial filter surface observation camera 88. For example, an area 330 on the operation screen 300 should display setting information of the image plane observation lens 86, that of the image plane observation camera 89, that of the adjustable field-of-view diaphragm 81, and an operation screen thereof.

In addition, an area 340 on the operation screen 300 should display, for example, setting information of the spatial filter surface observation lens 84, that of the spatial filter surface observation camera 88, that of rod-shaped light shielding objects 327, 328 of the spatial filter 45 and an operation screen thereof.

Figure 4:
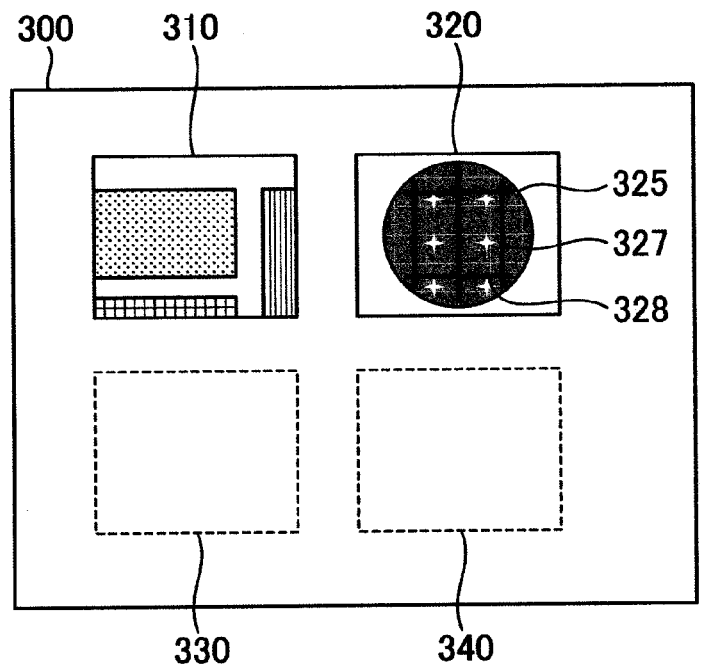
FIG. 4 is a diagram illustrating an example of a spatial filter setting screen according to a first embodiment of the present invention.

In a state shown in FIG. 4, the adjustable field-of-view diaphragm 81 is largely opened, and the field-of-view of the image plane observation camera 89 is limited by the size of the image sensor of the camera 89. Therefore, a plurality of patterns on the object to be inspected 10 are observed over the whole screen.

Meanwhile, the spatial filter surface observation camera 88 observes overlaid diffracted light beams 325 from a plurality of pattern regions. In this state, it is not easy to know which diffracted light beam 325 needs to be shielded to remove a pattern of the target region 200a (shown in FIG. 3). For this reason, in the prior art, it is necessary to repeat trial and error a plurality of times, and the settings of the light shielding objects 327, 328 of the spatial filter 45 require much time. Therefore, the optimization also becomes difficult.

In the first embodiment of the present invention, the adjustable field-of-view diaphragm 81 is adjusted so that only the target repetitive pattern 200a appears in the field-of-view on an image plane observation image for the adjustment of the spatial filter 45 (step 920), and the observation of the spatial filter surface image 320 in one-to-one correspondence to the target repetitive pattern 200a is enabled, which facilitates optimum settings of the light shielding objects 327, 328 of the spatial filter 45. The operator is allowed to manually set the light shielding objects 327, 328 of the spatial filter 45 through the operation section (light shielding condition setting unit) 130 and the control section (light shielding condition setting unit) 120. Incidentally, as described below, the light shielding objects 327, 328 of the spatial filter 45 can also be automatically set to be an optimum state.

Figure 5:
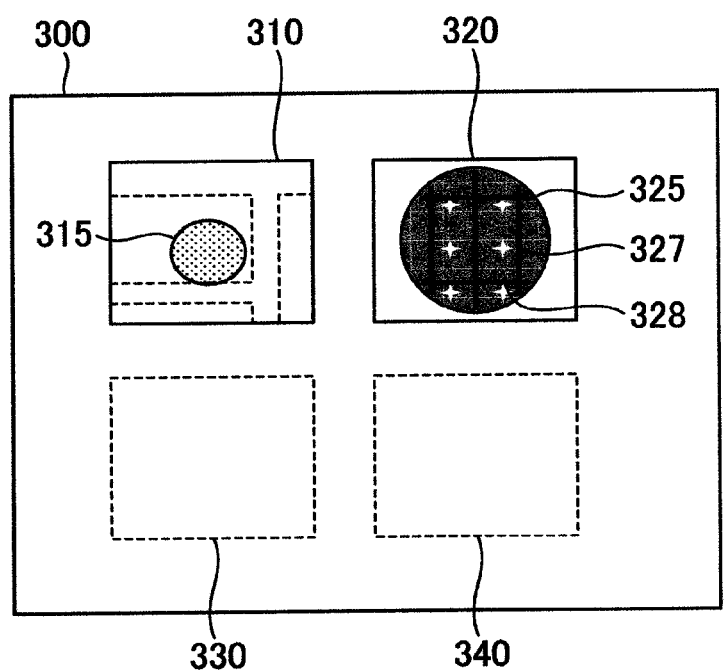
FIG. 5 is a diagram illustrating an example of a spatial filter setting screen according to the first embodiment of the present invention.

As shown in FIG. 5, narrowing the adjustable field-of-view diaphragm 81 makes it possible to cause only the repetitive pattern 200a to appear in a field-of-view 315 limited by the adjustable field-of-view diaphragm 81. In this case, the Fourier transform image 320 observed in the spatial filter surface is a Fourier image consisting only of the pattern 200a which appears in the field-of-view diaphragm 81.

Therefore, the light shielding objects 327, 328 of the spatial filter 45 are set in such a manner that the diffracted light beam 325 on this Fourier transform image 320 (step 930) is shielded. This makes it possible to cause the target pattern 200a to disappear.

By displaying images of the image plane observation camera 88 on the operation screen 300 of the operation section 130, when the spatial filter 45 is adjusted, whether or not bright spots of the diffracted light could be shielded can be determined by the spatial filter plane image 320. At the same time, whether or not the repetitive pattern 200*a* has disappeared can be determined by the image plane observation image 310 (step 940). Consequently, the operator can immediately determine that the settings of the spatial filter 45 are correct, and that the effects therefrom could be achieved.

Incidentally, although a circular aperture is shown as an example of the aperture of the field-of-view diaphragm 81 here, the shape of the aperture is not limited to a circle, and thus the aperture may have any shape. In general, a region in which a pattern exists is rectangular. Therefore, using a rectangular aperture makes it possible to provide a wide aperture region in the image plane, and has the advantage that the brightness of the spatial filter surface image can be easily achieved.

Figure 6:
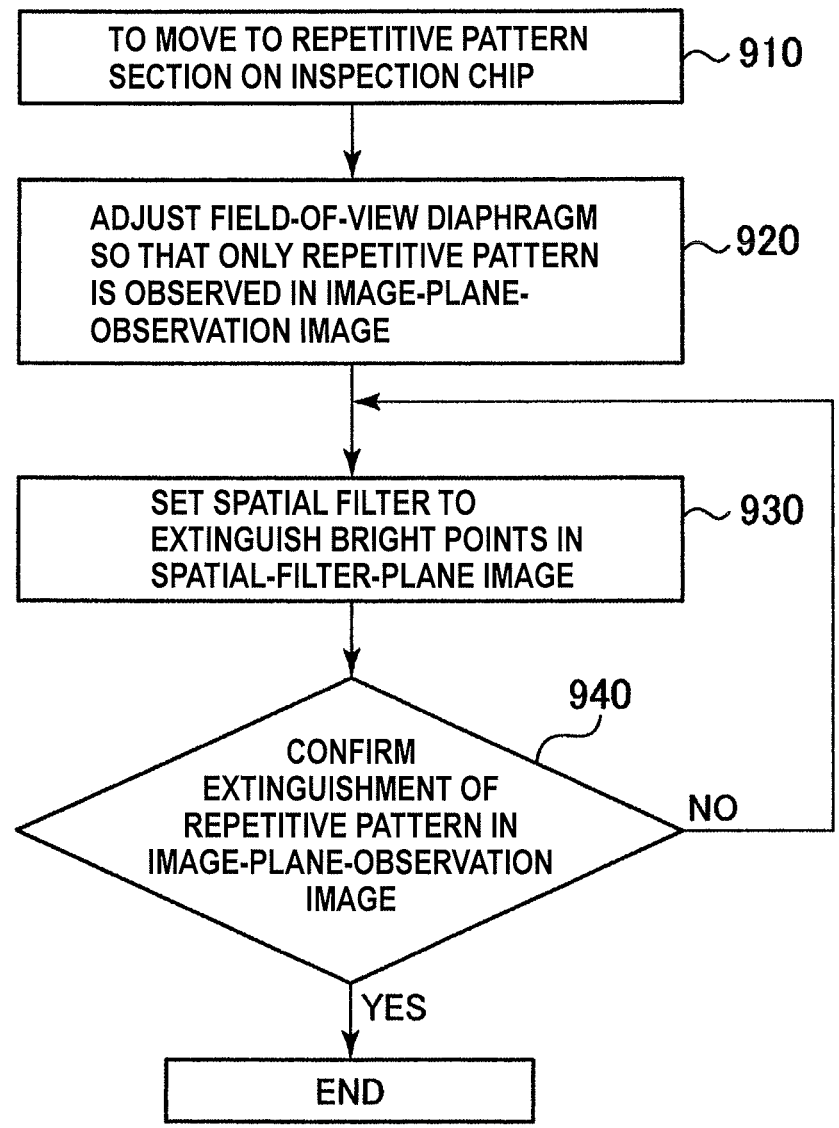
FIG. 6 is a flowchart illustrating an example of spatial filter setting steps according to the first embodiment of the present invention.
Figure 7:
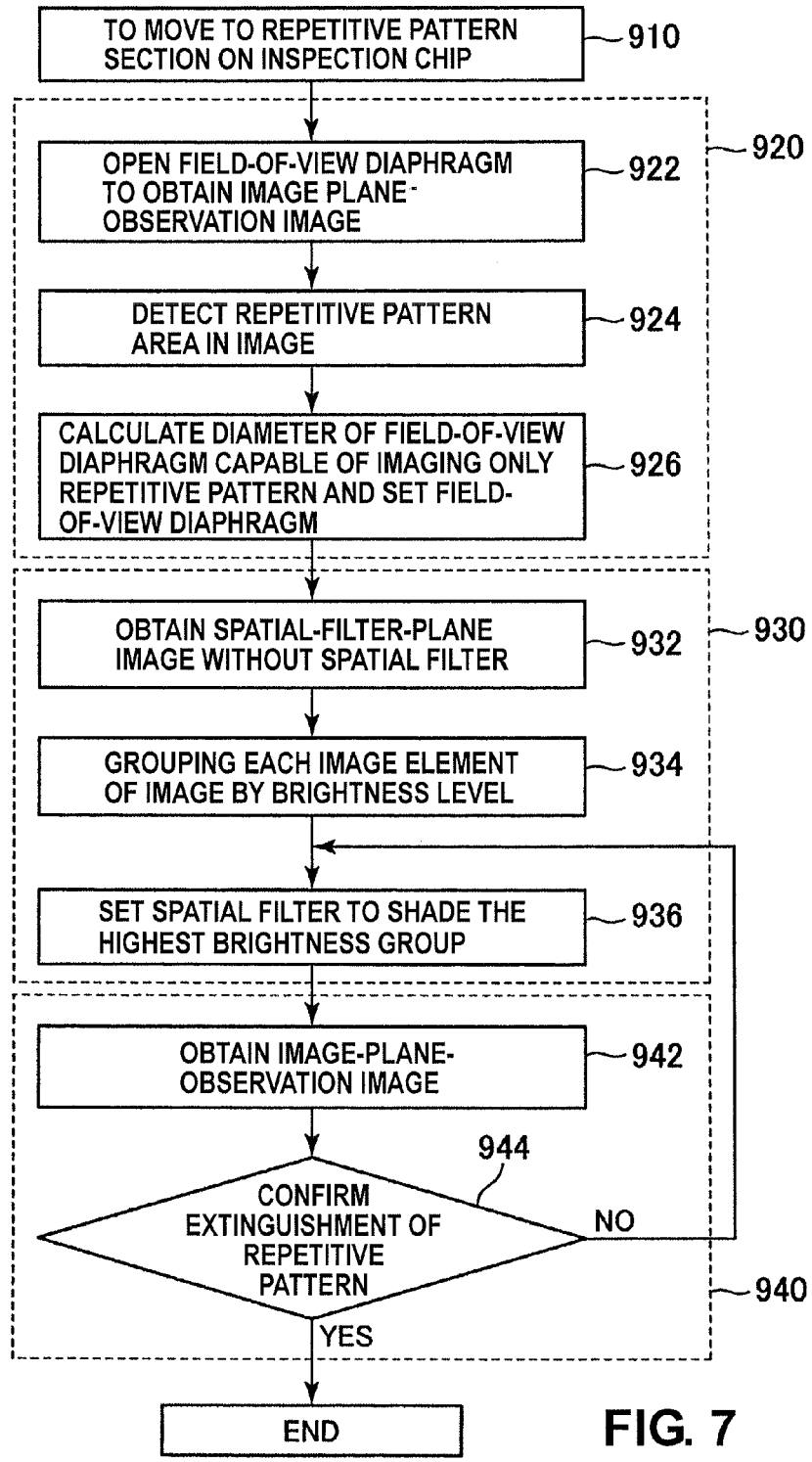
FIG. 7 is a flowchart illustrating an example of automation steps of spatial filter settings according to the first embodiment of the present invention.

Next, FIG. 7 illustrates further detailed steps of automating the settings of the spatial filter 45 described with reference to FIG. 6. Incidentally, an example shown in FIG. 7 illustrates in detail a flow in which in order to automate the steps, an image is captured, then processed, and a light shielding object of the spatial filter 45 is set. Processing for the automation is mainly performed by the control section 120.

In FIG. 7, the step 910 is similar to the step shown in FIG. 6. The step 920 is divided into image capturing (step 922), region extraction (step 924) by image processing, and calculation and setting of a field-of-view diaphragm diameter (step 926).

First, an image of the object to be inspected 10 is captured by use of the image plane observation camera 89 with the adjustable field-of-view diaphragm 81 opened (step 922). As with the image 310 shown in FIG. 4, an image in which a plurality of regions each having different pattern characteristics exist over the whole field-of-view of the camera is captured. A repetitive pattern in proximity to the center of the image is extracted from the image on the basis of pattern arrangement information stored in an internal storage unit of the control section 120 (step 924). An aperture diameter of the adjustable aperture diaphragm 81, which is required to shield light in the other regions, is calculated, and the diaphragm 81 is then moved to adjust the aperture diameter to the calculated value (step 926). The diaphragm 81 is controlled so as to achieve an aperture diameter set by an instruction signal of the control section 120.

The step 930 is divided into spatial filter surface image capturing (step 932), pixel brightness level classification (step 934) and spatial filter settings (step 936).

Figure 8A:
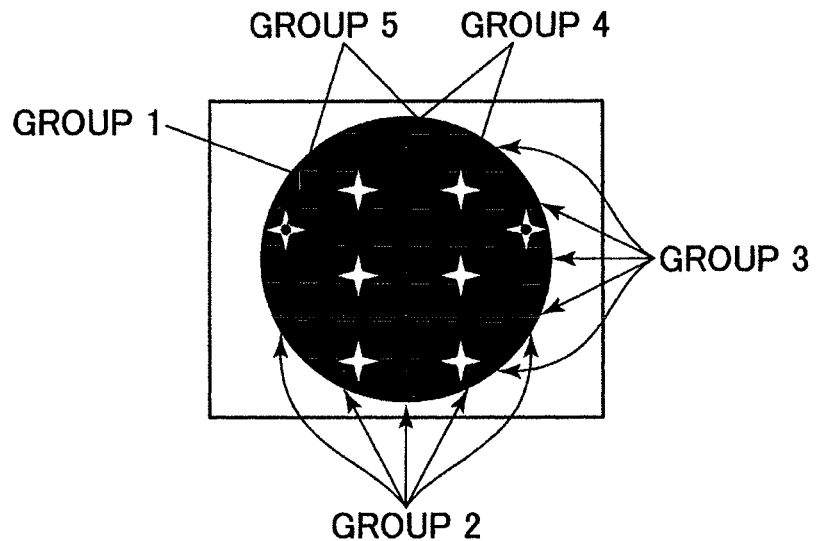
FIG. 8A is a diagram illustrating automation steps of spatial filter settings according to the first embodiment of the present invention.
Figure 8B:
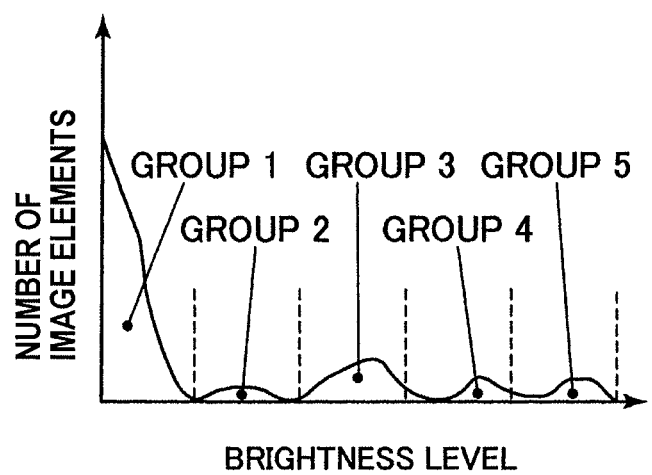
FIG. 8B is a chart illustrating automation steps of spatial filter settings according to the first embodiment of the present invention.

First, an image of the spatial filter surface is obtained by use of the spatial filter surface observation camera 88 without the light shielding objects 327, 328 of the spatial filter 45 (step 932). As shown in FIG. 8A, an image having bright spots (or lines) of the diffracted light 325 is obtained. The image is represented by a histogram as shown in, for example, FIG. 8B. Pixels of this image are classified into a plurality of groups according to the brightness level (pixel value).

For example, when an image is taken by a camera in which each pixel has 256 gray scales, the brightness level ranges from 0 to 255 gray scales. The pixels are classified on the histogram as follows: group 1—brightness level lower than 50; group 2—brightness level not lower than 50 and lower than 100; group 3—brightness level not lower than 100 and lower than 150; group 4—brightness level not lower than 150 and lower than 200; and group 5—brightness level not lower than 200 (step 934, FIG. 8B).

As shown in FIG. 8A, the background of the image is dark, and therefore belongs to the group 1. Bright spots and bright lines of diffraction components belong to the groups 2 to 5 according to each strength level. When the spatial filter 45 is set, first, the light shielding objects 327, 328 of the spatial filter are set in such a manner that the group 5, the brightness level of which is the highest, can be shielded (step 936). When the light shielding objects 327, 328 are set, for example, first, the light shielding object 327 is moved to a position at which the brightness level was the highest, and the light shielding object 327 is then set. After that, the light shielding object 328 is moved to a position at which the brightness level was the highest, and the light shielding object 328 is then set. Thus, the spatial filter 45 can be set. The movement control of the light shielding objects 327, 328 are carried out by the control section 120.

Next, the step 940 is divided into capturing of an image plane observation image (step 942) and determination whether or not an repetitive pattern exists (step 944). After the spatial filter 45 is set in the step 930, an image of the object to be inspected 10 is obtained by use of the image plane observation camera 89 (step 942).

Next, whether or not a repetitive pattern remains in the obtained image is determined (step 944). Whether or not a repetitive pattern exists may be determined by calculating a correlation value with respect to, for example, an image before the spatial filter 45 is put in (for example, obtaining after the step 926), and then by subjecting the correlation value to threshold value processing.

In addition, whether or not a repetitive pattern exists may be determined by extracting part of the image, by performing correlation calculation of the part with the whole image to generate a correlation value distribution, and then by subjecting the distribution to the threshold value processing; or after the image is Fourier transformed and is converted into a spatial frequency component, the component may be subjected to the threshold value processing.

When it is determined that a repetitive pattern remains, the process returns to the step 936, and the settings of the spatial filter 45 are further changed.

The spatial filter 45 is set in such a manner that in addition to the group 5 which has been light-shielded earlier, the group 4, the brightness level of which is the highest next to the group 5, can also be light-shielded. The same step is repeated until it is determined that no repetitive pattern remains. Then, when it is determined that no repetitive pattern remains, the settings of the spatial filter 45 end.

Incidentally, the example in which when the spatial filter 45 is set, light shielding is performed from the pixel group, the brightness of which is simply high, is shown. However, a distribution shape of the diffraction light components (points or lines) may be determined to change the priority order according to the distribution shape. For example, even if the brightness level is low, a priority is put on light-shielding of bright spots, or conversely a priority is put on removal of bright lines. Thus, changing the priority order according to the distribution shape makes it possible to cause the spatial filter 45 to function by priority for a region which requires sufficient inspection sensitivity.

As described above, according to the first embodiment of the present invention, the aperture diameter of the adjustable field-of-view diaphragm 81 is narrowed, the spatial filter screen from a pattern in a specific region is displayed on the screen (displayed on the operation screen of the operation section 130), and the light shielding objects 327, 328 of the spatial filter 45 are set so as to light-shield bright spots of diffracted light. Therefore, a defect inspecting method can be realized which enables the efficiency of spatial filter settings, and at the same time enables automation of the spatial filter settings. Also, a defect inspection system using the method can be realized.

Second Embodiment

Figure 10:
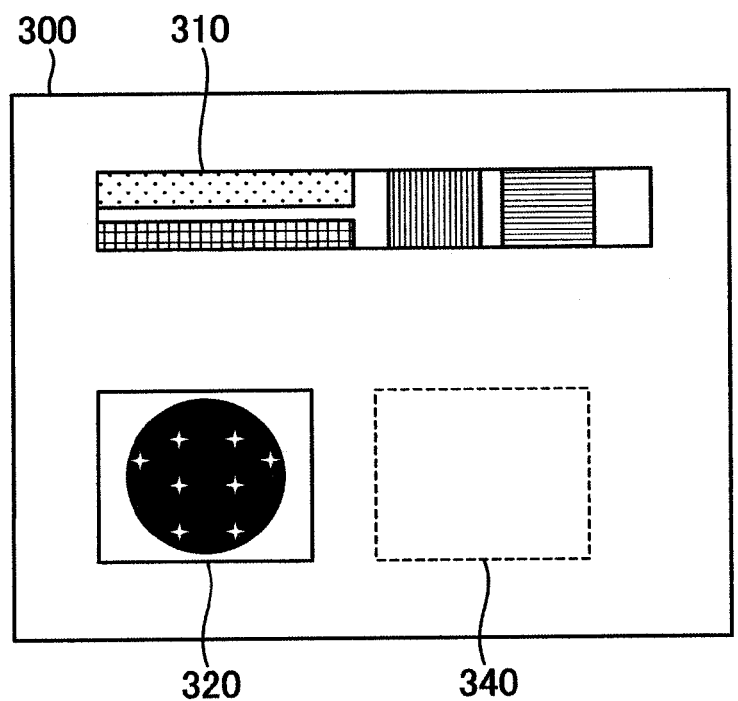
FIG. 10 is a diagram illustrating a spatial filter setting screen according to the second embodiment of the present invention.

Next, settings of a spatial filter in a defect inspection system, which is the second embodiment of the present invention, will be described with reference to FIGS. 9 and 10.

FIG. 9 illustrates steps of setting a spatial filter in the second embodiment of the present invention. FIG. 10 illustrates a spatial filter setting screen 300 in the second embodiment of the present invention. The overall configuration of the defect inspection system is identical to that in the example shown in FIG. 1.

In the second embodiment, the chip 200 on the object to be inspected 10 is scanned in one line, and the spatial filter 45 is set by use of the image 310 (FIG. 10) captured by the sensor 70 and the image 320 of the spatial filter surface which is taken by adding up in succession during scanning. With respect to the size of the image 310, a direction orthogonal to the scan direction (up and down direction of FIG. 10) corresponds to the width of the field-of-view of the sensor 70, and the scan direction is at least one chip of the chip 200 of the object to be inspected 10.

When these images are captured, the adjustable field-of-view diaphragm 81 of the observation optical system 80 is set to the maximum with the beam splitter 50 put in the optical path between the sensor 70 and the detection lens 40 (step 1010), and the images are then taken by the sensor 70 and the spatial filter surface observation camera 88 (step 1020).

Keeping the adjustable field-of-view diaphragm 81 open at the maximum level enables the observation optical system 80 to image the widest imaging area of the field-of-view of the sensor 70. This makes it possible to put a spatial filter plane image including diffracted light beams from many regions displayed in the image 310 in one piece of image 320.

Checking the image 310 as to whether or not a region to be inspected is covered, and then setting the spatial filter 45 with reference to the image 320 in such a manner that a diffracted light beam, the brightness of which is high, is shielded, enables the settings of the spatial filter 45 corresponding to a plurality of regions. When bright spots to be light-shielded by the spatial filter are selected, as with the first embodiment, pixels of the spatial filter surface image are grouped according to the brightness level (step 1030), and a group, the brightness of which is high, is light-shielded by priority (step 1040). This enables spatial filter settings which remove, by priority, a repetitive pattern extending over the wide area.

After the settings of the spatial filter 45 are determined, the same position is line-scanned again to obtain an inspection image, and then to determine whether or not the repetitive pattern has been removed (step 1050).

When it is determined that there remains an unremoved repetitive pattern, the spatial filter 45 is set again in such a manner that a pixel group, the brightness of which is the next highest to the pixel group which has been light-shielded earlier, is also light-shielded, and then an inspection image is checked. Repeating these steps enables optimum settings of the spatial filter 45. Employment of this method also enables the operator to perform automatic settings of the spatial filter 45 corresponding to a region to be line-scanned only by instructing the region.

Incidentally, in the example described above, when the image 320 is captured, the images are successively taken and accumulated during one line scanning. However, the time taken for one line scanning may be divided into short lengths of time to take many images, and then to subject the images to peak hold operation, addition, averaging and the like, thereby obtaining a spatial filter surface image corresponding to the final one line scanning.

In addition, when the automatic settings of the spatial filter 45 is performed, the distribution on the spatial filter surface of scattering diffracted light from a pattern may be calculated by use of design data of the pattern on the object to be inspected, and by use of parameters of the illumination optical system and detection optical system of the inspection system (NA of illumination, an azimuth, an incident angle, NA of the detection lens and the like), so that a comparison is made with an image taken by the spatial filter surface observation camera to verify the distribution, and thereby to determine spatial filter settings.

Figure 11:
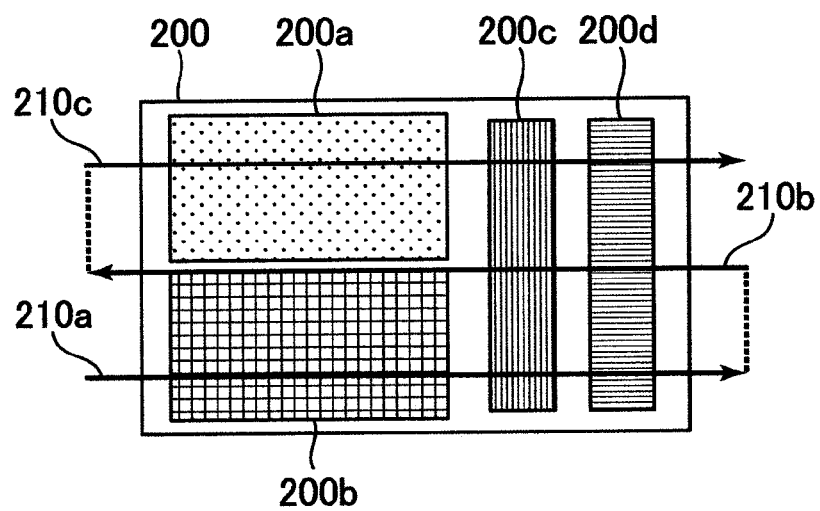
FIG. 11 is a diagram illustrating spatial filter settings according to the second embodiment of the present invention.

When the most optimum settings of the spatial filter are made for the whole chip 200 on the object to be inspected 10, scanning is performed over the whole chip 200 (210a to 210c) to obtain line scan images 410a to 410c and spatial filter surface image 420a to 420c corresponding thereto as shown in FIG. 11.

Figure 12:
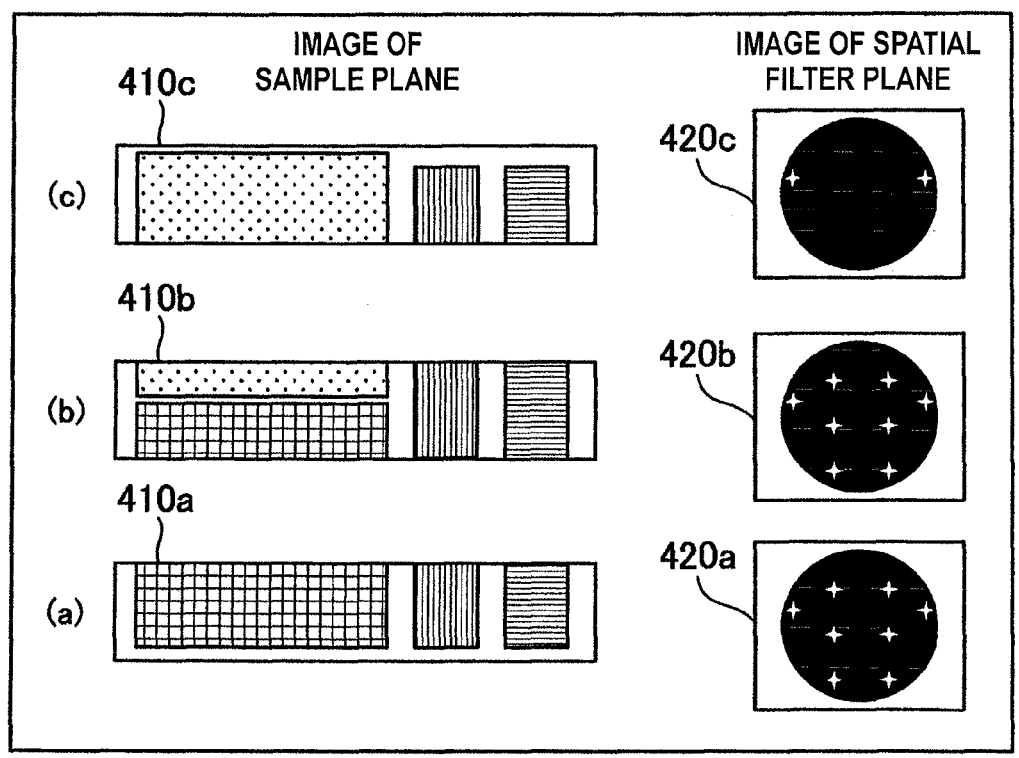
FIG. 12 is a diagram illustrating an example of spatial filter setting according to the second embodiment of the present invention.

The spatial filter 45 is set while the images captured as above are displayed on the setting screen as shown in FIG. 12. Setting the spatial filter 45 on a scan line basis by use of these images according to the above-described steps makes it possible to achieve spatial filter settings which enable efficient inspection of the whole chip 200.

In addition, if it is desirable that spatial filter settings should not be changed on a scan line basis for the purpose of achieving high throughput or the like, spatial filter surface images 420a to 420c are handled as one image to group the pixels thereof according to the brightness level, and then to set the spatial filter in such a manner that a group, the brightness of which is high, is light-shielded by priority.

This enables settings of the spatial filter 45 which have average effects on a plurality of scan lines.

Effects similar to those of the first embodiment can be achieved also in the second embodiment of the present invention.

DESCRIPTION OF REFERENCE NUMERALS

10 Object to be inspected (sample, substrate, wafer)
20 Illumination light
30 Illumination optical system (including light source)
40 Detection lens
45 Spatial filter
50 Beam splitter
70 Sensor
80 Observation optical system
81 Observation optical system field-of-view diaphragm
88 Spatial filter plane observation camera
89 Image plane observation camera
100 Detection optical system
110 Stage
120 Control section
130 Operation section
140 Image processing section
300 Operation screen
310 Image of image plane observation camera
320 Image of spatial filter plane observation camera
325 Diffracted light
327, 328 Light shielding object of spatial filter

The invention claimed is:

1. A defect inspection system comprising:
   an optical system configured to irradiate an object to be inspected with light;
   a detection lens configured to image reflected and scattered light from the object to be inspected;
   a spatial filter which is disposed on a spatial frequency plane of the detection lens, the spatial filter being configured to selectively transmit diffracted light;
   an image sensor which is disposed on an image plane of the detection lens, the image sensor being configured to photoelectrically convert the image of the reflected and scattered light;
   an image processing section which is configured to subject the image captured by the image sensor to comparison processing to detect a foreign matter or a pattern defect on the object to be inspected;
   an observation optical system which is capable of substantially concurrently observing the image plane of the detection lens and a spatial filter plane corresponding to the image plane; and
   a light shielding condition setting system which is provided with a spatial filter setting screen, the spatial filter setting screen being capable of substantially concurrently displaying an image of the surface of the object to be inspected and an image of a spatial filter plane corresponding to the image, the light shielding condition setting system being configured to set light shielding conditions of the spatial filter.

2. The defect inspection system according to claim 1, further comprising:
   an adjustable field-of-view diaphragm which is disposed in the observation optical system, the adjustable field-of-view diaphragm being configured to limit a field-of-view of the image plane.

3. The defect inspection system according to claim 2, wherein:
   the light shielding condition setting system is configured to adjust the aperture size of the adjustable field-of-view diaphragm, display a region formed with a specific pattern among a plurality of patterns formed on the surface of the object to be inspected on the image plane observation image of the spatial filter setting screen, and display an observation image of the spatial filter plane on the spatial filter setting screen.

4. The defect inspection system according to claim 1, wherein
   the light shielding condition setting system is configured to obtain an image of the spatial filter plane without light shielding objects in the spatial filter from the observation optical system, classify pixels of the image of the spatial filter obtained from the observation optical system into a plurality of groups of brightness levels, and set the light shielding objects to the spatial filter to shield a group having highest brightness level in the plurality of groups of brightness levels.

5. A defect inspection system comprising:
   a stage which is configured to hold and move an object to be inspected;
   an optical system configured to irradiate an object to be inspected with light;
   a detection lens configured to image reflected and scattered light from the object to be inspected;
   a spatial filter which is disposed on a spatial frequency plane of the detection lens, the spatial filter being configured to selectively transmit diffracted light;
   an image sensor which is disposed on an image plane of the detection lens, the image sensor being configured to photoelectrically convert the image of the reflected and scattered light;
   an image processing section which is configured to subject the image captured by the image sensor to comparison processing to detect a foreign matter or a pattern defect on the object to be inspected; and
   an observation optical system which is capable of substantially concurrently observing the image plane of the detection lens and a spatial filter plane corresponding to the image plane.

6. The defect inspection system according to claim 5, further comprising
   a control section, and
   an operation section,
   wherein the control section is configured to move the stage to obtain a spatial filter plane image of a region instructed by the operation section, and set positions of light shielding objects of the spatial filter in such a manner that part, the brightness of which is a predetermined brightness level or higher, is light-shielded.

7. The defect inspection system according to claim 6, wherein:
   the control section is configured to move the stage to obtain a spatial filter plane image, set positions of the light shielding objects in such a manner that the part, the brightness of which is the predetermined brightness level or higher, is light-shielded, then further to move the stage to obtain an image of the surface of the object to be inspected, determine whether or not a repetitive pattern exists in the region instructed by the operation section, and if it is determined that there remains a repetitive pattern, set positions of light shielding objects of the spatial filter in such a manner that part, the brightness of which is higher than or equal to a second level that is lower than the predetermined level, is further light-shielded.

8. The defect inspection system according to claim 5, further comprising:
   a light shielding condition setting system which is provided with a spatial filter setting screen, the spatial filter setting screen being capable of substantially concurrently displaying an image of the surface of the object to be inspected and an image of a spatial filter plane corresponding to the image, the light shielding condition setting system being configured to set light shielding conditions of the spatial filter,
   wherein the light shielding condition setting system is configured to obtain an image of the spatial filter plane without light shielding objects in the spatial filter from the observation optical system, classify pixels of the image of the spatial filter obtained from the observation optical system into a plurality of groups of brightness levels, and set the light shielding objects to the spatial filter to shield a group having highest brightness level in the plurality of groups of brightness levels.

9. A defect inspection method comprising the steps of:
   irradiating an object to be inspected with light;
   collecting reflected and scattered light from the object to be inspected by use of a detection lens, and imaging light, which is selectively transmitted through a spatial filter disposed in the detection lens, on an image sensor;
   substantially concurrently observing an image plane of the detection lens and a spatial filter plane corresponding to the image plane;

displaying a region formed with a specific pattern among a plurality of patterns formed on the surface of the object to be inspected and a spatial filter plane corresponding to the region formed with the specific pattern on a spatial filter setting screen, and setting light shielding conditions of the spatial filter;

obtaining an image of the object to be inspected by use of the image sensor under the setting conditions;

subjecting the captured image to comparison processing; and detecting, based on the comparison processing, a foreign matter or a pattern defect on the object to be inspected.

10. The defect inspection method according to claim 9, wherein:

an adjustable field-of-view diaphragm, which is disposed in the observation optical system, and limits a field-of-view of the image plane, is adjusted to display the region formed with the specific pattern, and a spatial filter plane corresponding to the region formed with the specific pattern, on the spatial filter setting screen display.

11. The defect inspection method according to claim 10, wherein:

the object to be inspected is moved to obtain a spatial filter plane image of the region formed with the specific pattern, and positions of light shielding objects of the spatial filter are set in such a manner that part, the brightness of which is a predetermined brightness level or higher, is light-shielded.

12. The defect inspection method according to claim 11, wherein:

the object to be inspected is moved to obtain a spatial filter plane image, positions of the light shielding objects are set in such a manner that the part, the brightness of which is the predetermined brightness level or higher, is light-shielded in the region formed with the specific pattern, then the object to be inspected is further moved to obtain an image of the surface of the object to be inspected, whether or not a repetitive pattern exists in the region formed with the specific pattern is determined, and if it is determined that there remains a repetitive pattern, positions of the light shielding objects of the spatial filter are set in such a manner that part, the brightness of which is higher than or equal to a second level that is lower than the predetermined level, is further light-shielded.

13. The defect inspection method according to claim 9, wherein the light shielding condition setting system is configured to obtain an image of the spatial filter plane without light shielding objects in the spatial filter from the observation optical system, classify pixels of the image of the spatial filter obtained from the observation optical system into a plurality of groups of brightness levels, and set the light shielding objects to the spatial filter to shield a group having highest brightness level in the plurality of groups of brightness levels.

14. A defect inspection system comprising:

an optical system configured to irradiate an object to be inspected with light;

a detection lens configured to image reflected and scattered light from the object to be inspected;

a spatial filter which is disposed on a spatial frequency plane of the detection lens, the spatial filter being configured to selectively transmit diffracted light;

an image sensor which is disposed on an image plane of the detection lens, the image sensor being configured to photoelectrically convert the image of the reflected and scattered light;

an image processing section which is configured to subject the image captured by the image sensor to comparison processing to detect a foreign matter or a pattern defect on the object to be inspected;

an observation optical system which is capable of substantially concurrently observing the image plane of the detection lens and a spatial filter plane corresponding to the image plane; and an adjustable field-of-view diaphragm which is disposed in the observation optical system, the adjustable field-of-view diaphragm being configured to limit a field-of-view of the image plane.

15. The defect inspection system according to claim 14, further comprising:

a light shielding condition setting system which is provided with a spatial filter setting screen, the spatial filter setting screen being capable of substantially concurrently displaying an image of the surface of the object to be inspected and an image of a spatial filter plane corresponding to the image, the light shielding condition setting system being configured to set light shielding conditions of the spatial filter.

16. The defect inspection system according to claim 14, further comprising:

a light shielding condition setting system which is provided with a spatial filter setting screen, the spatial filter setting screen being capable of substantially concurrently displaying an image of the surface of the object to be inspected and an image of a spatial filter plane corresponding to the image, the light shielding condition setting system being configured to set light shielding conditions of the spatial filter, wherein the light shielding condition setting system is configured to obtain an image of the spatial filter plane without light shielding objects in the spatial filter from the observation optical system, classify pixels of the image of the spatial filter obtained from the observation optical system into a plurality of groups of brightness levels, and set the light shielding objects to the spatial filter to shield a group having highest brightness level in the plurality of groups of brightness levels.

17. A defect inspection method comprising the steps of:

irradiating an object to be inspected with light;

collecting reflected and scattered light from the object to be inspected by use of a detection lens while the object to be inspected is moved;

imaging light, which is selectively transmitted through a spatial filter disposed in the detection lens, on an image sensor to take the image;

at the same time, using the image sensor to take an image of the spatial filter plane corresponding to an image plane of the detection lens;

displaying an image of a pattern formed on the surface of the image-taken object to be inspected and the image of the spatial filter plane on a spatial filter setting screen, and setting light shielding conditions of the spatial filter;

obtaining an image of the object to be inspected by use of the image sensor under the set conditions again while the object to be inspected is moved; and subjecting the captured image to comparison processing; and detecting, based on a result of the comparison processing, a foreign matter or a pattern defect on the object to be inspected.

18. The defect inspection method according to claim 17, wherein
the light shielding condition setting system is configured to obtain an image of the spatial filter plane without light shielding objects in the spatial filter from the observation optical system, classify pixels of the image of the spatial filter obtained from the observation optical system into a plurality of groups of brightness levels, and set the light shielding objects to the spatial filter to shield a group having highest brightness level in the plurality of groups of brightness levels.

\* \* \* \* \*